United States Patent [19]

Athans

[11] Patent Number: 4,593,698

[45] Date of Patent: Jun. 10, 1986

[54] ELECTROCARDIOGRAPH SENSOR POSITIONING DEVICE AND METHOD

[76] Inventor: Robert J. Athans, 21 Meadow Ave., Bronxville, N.Y. 10708

[21] Appl. No.: 673,668

[22] Filed: Nov. 21, 1984

[51] Int. Cl.<sup>4</sup> ............................................. A61B 5/04
[52] U.S. Cl. ................................. 128/644; 128/696; 128/774
[58] Field of Search ............... 128/696, 639, 644, 774; 604/116; 33/511

[56] References Cited

U.S. PATENT DOCUMENTS

| | | | |
|---|---|---|---|
| 2,245,350 | 6/1941 | Marshall | 604/116 X |
| 4,033,333 | 7/1977 | De Salvo et al. | 128/639 |
| 4,121,575 | 10/1978 | Mills et al. | 128/644 |
| 4,202,344 | 5/1980 | Mills et al. | 128/644 |
| 4,262,424 | 4/1981 | Hornbeck | 33/511 |
| 4,312,363 | 1/1982 | Rothfuss et al. | 128/774 |
| 4,432,368 | 2/1984 | Russek | 128/644 |
| 4,498,480 | 2/1985 | Mortensen | 128/644 |

Primary Examiner—Edward M. Coven
Attorney, Agent, or Firm—Rodman & Rodman

[57] ABSTRACT

The electrocardiograph sensor positioning device includes a pair of sensor locating members that are angularly adjustable with respect to each other to a determinable angular position. Cooperative indicia means provided on each of the sensor locating members furnish an indication of the relative angular position therebetween. Each of the sensor locating members defines a plurality of location zones for positioning of the electrocardiograph sensors and indicia means are provided alongside the location zone to determine the precise location of the electrocardiograph sensors when they are positioned in the location zones. The electrocardiograph sensor positioning device thus permits the establishment of reference paths on the human anatomy which are used to locate the positions of the electrocardiograph sensors. The size and extent of the reference paths and the pivotal arrangement of one of the sensor locating members permits adaptation of the device to a relatively wide range of anatomical size and shape regardless of sex.

20 Claims, 6 Drawing Figures

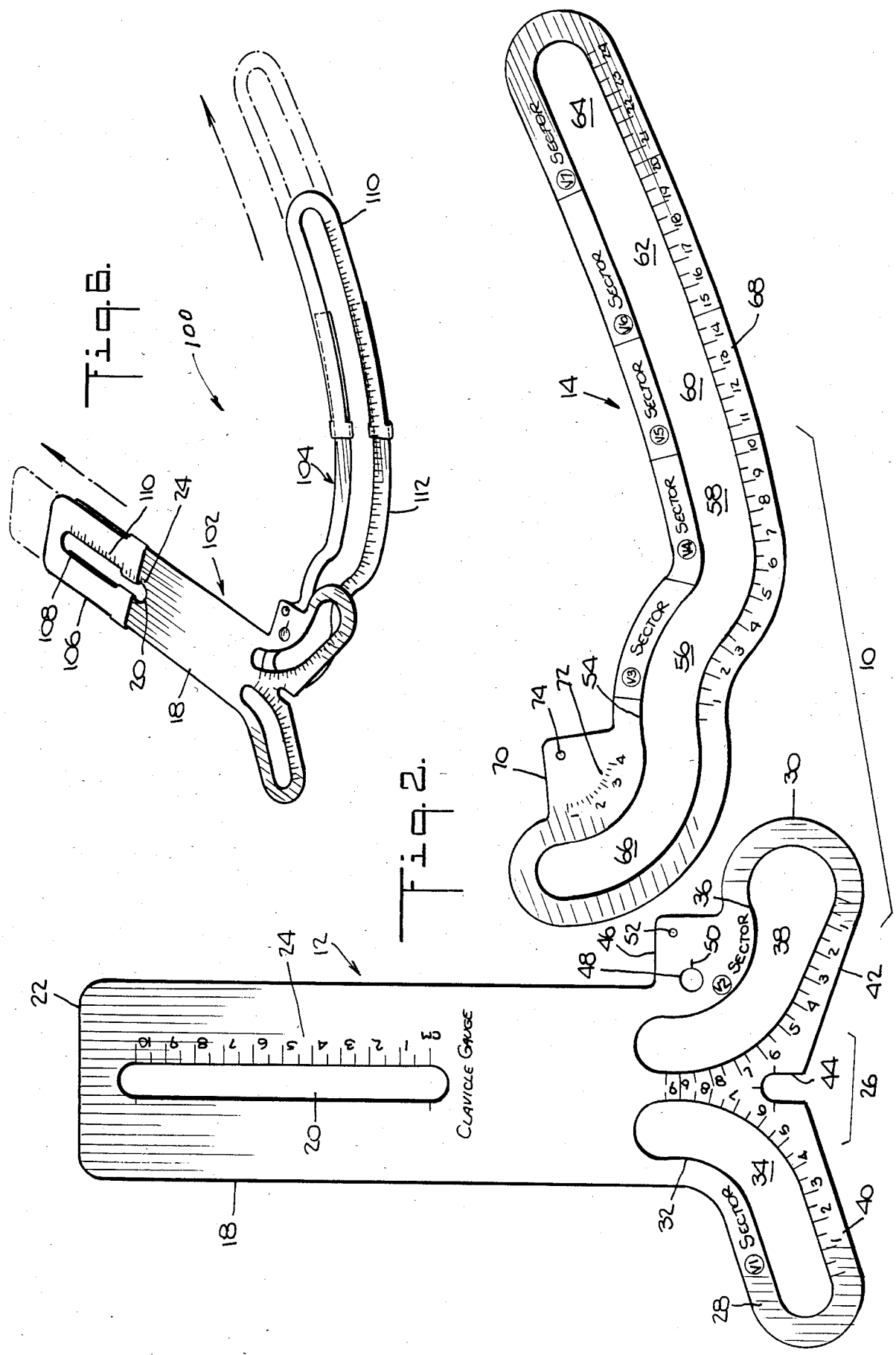

ELECTROCARDIOGRAPH SENSOR POSITIONING DEVICE AND METHOD

BACKGROUND OF THE INVENTION

This invention relates to electrocardiography, and more particularly to a positioning device for electrocardiograph sensors that provide a record of the precise location of the sensors on an individual.

In order to take an electrocardiogram recording, electrocardiograph sensors or exploration electrodes are placed on an individual's chest in the vicinity of the heart. The positioning of such electrodes is usually made pursuant to instructions of the instrument manufacturer and the skill and judgment of the person administering the electrocardiogram.

If an individual is to have more than one electrocardiogram taken at periodic intervals, it is desirable that each recording be taken with the exploration electrodes in the same position as the previous recording. A comparison of one electrocardiogram trace with another electrocardiogram trace then becomes more meaningful.

Unfortunately the location of exploration sensors in identical previous positions would require that the individual be tatooed or otherwise marked with the previous position, an impractical and unappealing prospect.

Attempts to deal with the problem of providing a consistent location for electrocardiograph sensors have not yielded an adequate solution.

For example, U.S. Pat. Nos. 4,121,575 and 4,202,344 show an elastic belt-like chest piece used in electrocardiography which has a vertical mark for indicating the mid-chest or mid-sternum and a horizontal mark for indicating the mid-nipple line. However the chest piece, which has six electrode positions, is stretched according to the size of the patient and cannot be otherwise oriented for purposes of exactly locating an electrocardiograph sensor in a repeatable position. Furthermore, these devices do not furnish data for recording the precise electrode positions during the taking of an electrocardiogram.

Other known electrode placement devices such as shown in U.S. Pat. Nos. 4,432,368; 4,457,309; 3,409,007; 3,476,104 and 4,033,303 are intended to facilitate placement of electrodes on an individual but do not deal with the problem of precisely locating such electrodes in repeatable positions on an individual.

In addition to determining repeatable positions for electrode sensors, it is important that the sensors be placed at predetermined locations on the anatomy. Otherwise deviations in an anticipated range of magnitude of electrical potential that have nothing to do with the condition of the heart will occur. A misplacement of the electrode away from a desired electrode location can thus lead to a faulty analysis of an individual's heart condition. Consequently a primary objective in electrocardiography is to precisely locate the electrode sensors in proximity to well defined anatomic landmarks. Once this has been accomplished, more meaningful data can be derived from the electrical potentials of electrocardiograph sensors.

It is thus desirable to provide an electrocardiograph sensor positioning device that provides data which assures repeatable locations of electrode sensors during subsequent electrocardiographic examinations and which establishes a location path for locating the electrodes in desired predetermined positions.

OBJECTS AND SUMMARY OF THE INVENTION

Among the several objects of the invention may be noted the provision of a novel electrocardiograph sensor positioning device, a novel electrocardiograph sensor positioning device that provides data for indicating the exact locations of electrocardiograph sensors that are positioned on an individual, a novel electrocardiograph sensor positioning device that can be used on persons with relatively small body structures as well as persons with relatively large body structures, a novel electrocardiograph sensor positioning device that can be retained by a patient after he has had an electrocardiograph examination and which provides a record of the exact locations of the electrocardiograph sensors for future reference on subsequent electrocardiographic examinations, a novel disposable electrocardiograph sensor positioning device, a novel low cost electrocardiograph sensor positioning device and a novel method of locating electrocardiograph sensors on an individual.

Other objects and features will be in part apparent and in part pointed out hereinafter.

In accordance with the present invention, an electrocardiograph sensor positioning device includes first and second sensor locating members that are angularly adjustable with respect to each other to a determinable angular position. Indicia means provided on the first and second sensor locating members provide an indication of the angular position to which the sensor locating members are adjusted. Each of the sensor locating members also includes zone locating means that define location zones which accommodate the electrocardiograph sensors.

The location zones also function as pathways which align with predetermined anatomic landmarks on a patient to assure precise location of the electrocardiograph sensors in a desired repeatable position. Repeatable location of the electrocardiograph sensors is accomplished through the provision of zone indicia means at the zone locating means which indicate the respective locations of the electrocardiograph sensors when such sensors are positioned in the respective location zones.

Preferably the first and second sensor locating members are pivoted to each other to provide a range of adjustability that permits adaptation of the device to patients of relatively small body structure as well as patients of relatively large body structure. The electrocardiograph sensor positioning device is thus adequate for use on patients of any size, sex or shape.

One of the sensor locating members includes registering means that permits positioning thereof in a predetermined aligned position. The registering means also includes an indicating arrangement that provides data for assuring a repeatable location of the sensor locating member in the predetermined aligned position. If desired, any one of the locating members can be formed as an extendable member.

The electrocardiograph sensor positioning device is thus used to locate electrocardiograph sensors on the human anatomy by establishing a longitudinal reference between two anatomical landmarks on an individual. An origin of the longitudinal reference is determined which locates a first plurality of location zones for the electrocardiograph sensors.

A second reference path is then established based on other anatomical landmarks and indicates a location zone for further electrocardiograph sensors. The second reference path is established after one of the sensor locating members is placed in a fixed position and the other of the sensor locating members is moved to a predetermined anatomical landmark area.

The invention accordingly comprises the constructions and methods hereinafter described, the scope of the invention being indicated in the claims.

DESCRIPTION OF THE DRAWINGS

In the accompanying drawings, in which several embodiments of the invention are illustrated.

FIG. 2 is an exploded view thereof;

Corresponding reference characters indicate corresponding parts throughout the several views of the drawings.

DETAILED DESCRIPTION OF THE INVENTION

Figure 1:
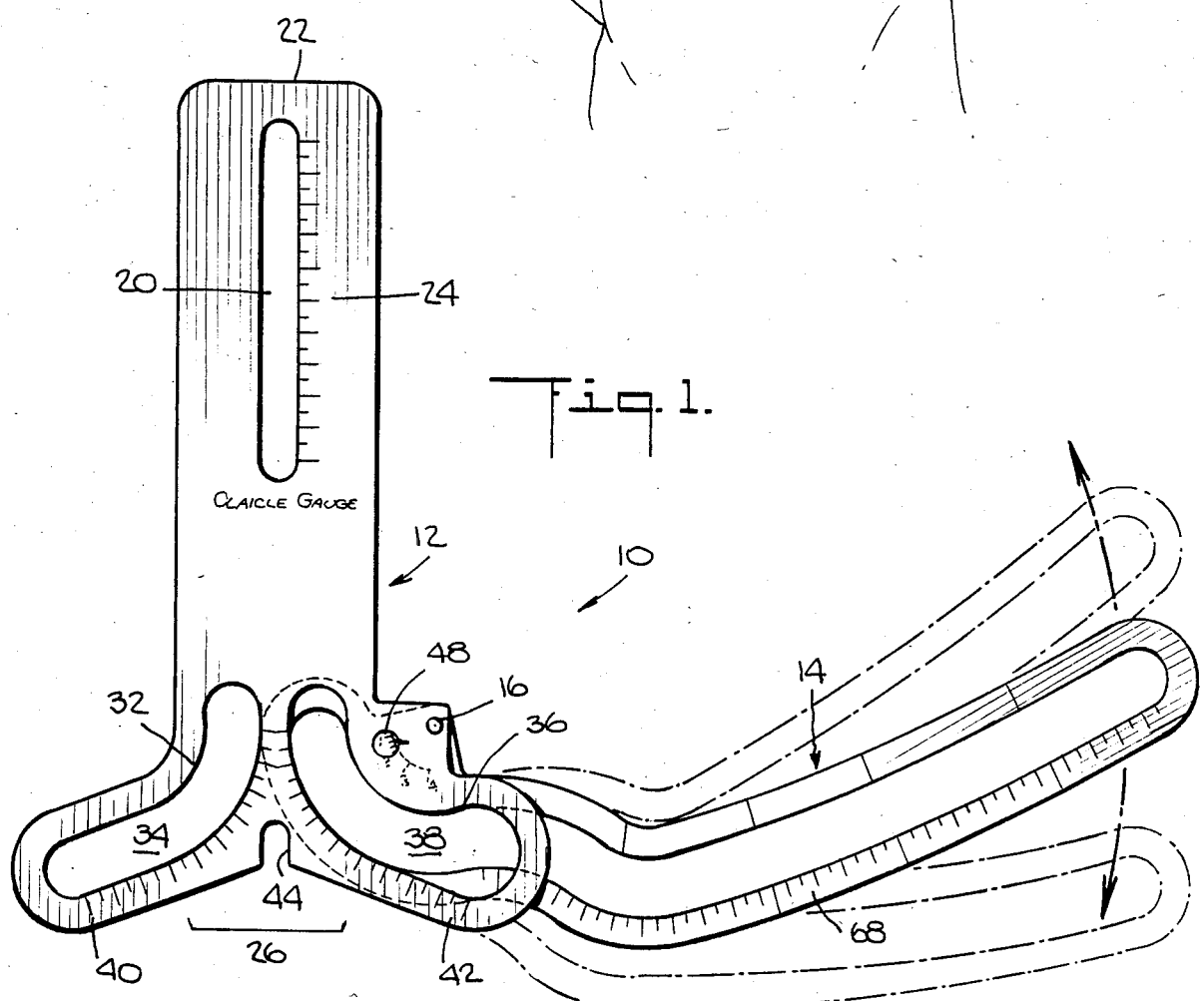
FIG. 1 is a plan view of an electrocardiograph sensor positioning device incorporating one embodiment of the invention.
Figure 4:
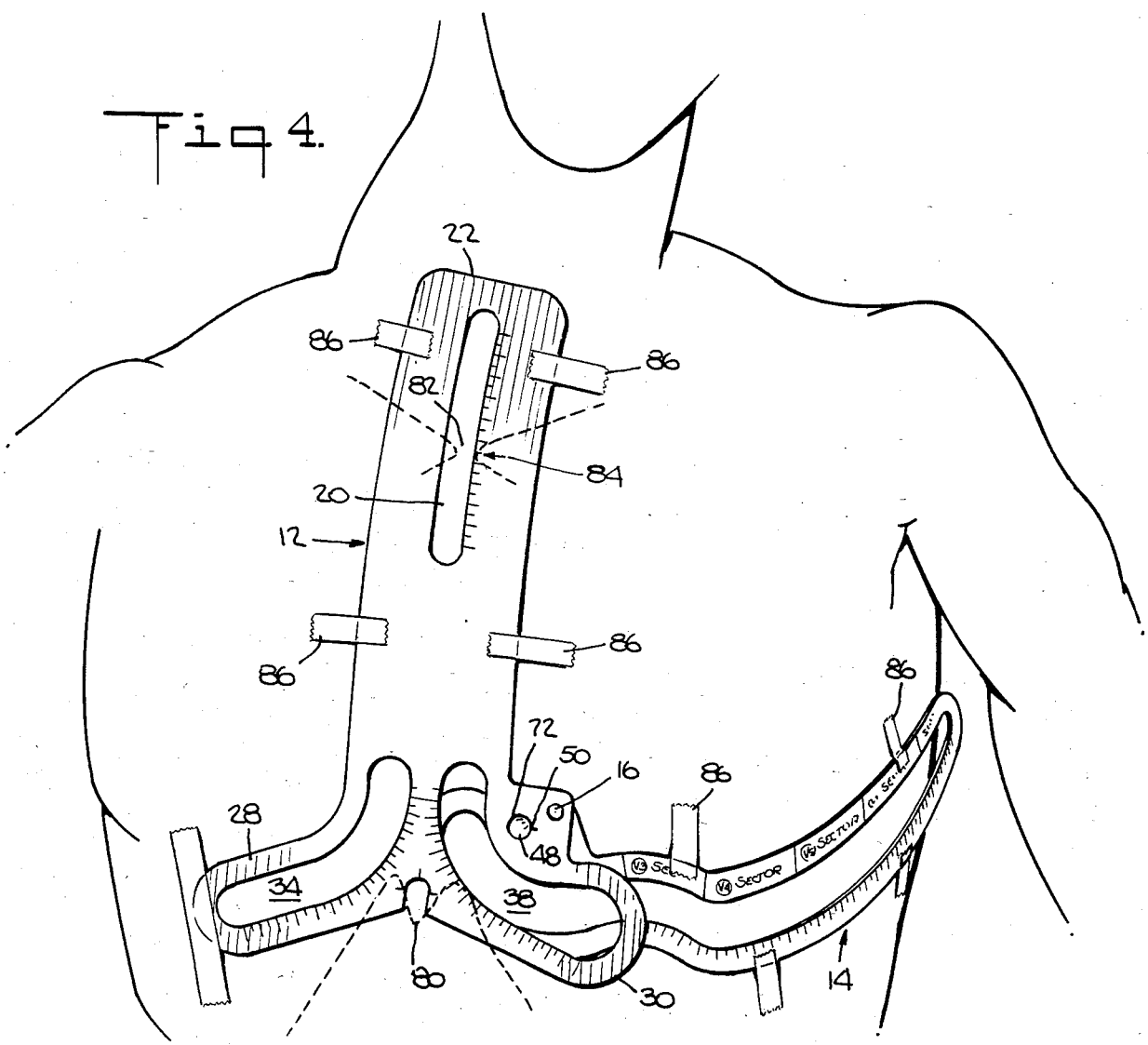
FIG. 4 shows the electrocardiograph sensor positioning device located on an individual.
Figure 5:
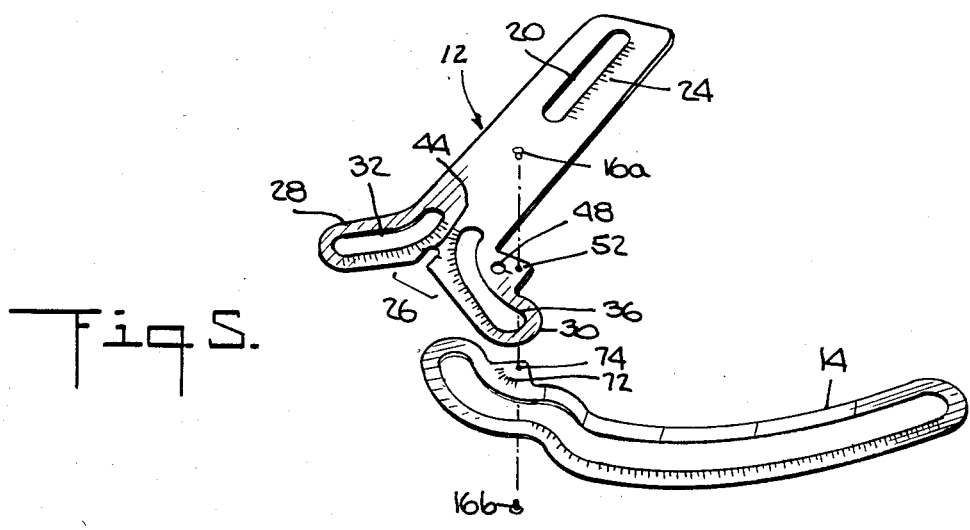
FIG. 5 shows the component parts of the electrocardiograph sensor positioning device prior to pivotal securement; and, FIG. 6 shows another embodiment of the invention.

An electrocardiograph sensor positioning device incorporating a preferred embodiment of the invention is generally indicated by the reference number 10 in FIG. 1. The device 10 comprises a pair of sensor locating members 12 and 14 moveable with respect to each other about a pivot 16 formed of pivot pieces 16a and 16b as shown in FIG. 5. The locating members 12 and 14 are preferably formed of a non-conductive flexible material such as plastic or paper having a thickness which permits such locating members to bend and conform to the curvature of the human anatomy at a precordial location such as shown in FIG. 4.

As most clearly shown in FIG. 2, the sensor locating member 12 has an elongated main section 18 that is formed with a relatively narrow slot 20 extending toward an end portion 22 of the main section 18. Indicia means such as a measurement scale 24 is provided alongside the slot 20. Preferably the measurement scale 24 is graduated in centimeters.

A base portion 26 of the main section 18 includes a pair of diverging zone sections 28 and 30. The zone section 28 includes a curved slot 32 defining a zone or pathway 34, whereas the zone section 30 includes an oppositely curved slot 36 defining a zone or pathway 38. Measurement scales 40 and 42 are provided alongside the respective slots 32 and 36.

A sternum notch register 44 provided intermediate the diverging zone sections 28 and 30 is colinear with the narrow slot 20. The sternum notch register 44 cooperates with the slot 20 to form a clavicle gauge based on indicated readings from the measurement scale 24.

The sensor locating member 12 also includes a flange portion 46 adjacent the curved slot 36. A scale opening 48 having an indicia line 50 is provided on the flange portion 46, and a pivot opening 52 is spaced from the scale opening 48.

The sensor locating member 14, which is elongated with some slight curves, is formed with a correspondingly shaped slot 54 that defines location zones 56, 58, 60, 62 and 64. The location zones 56, 58, 60, 62 and 64 collectively form a continuous pathway having a clearance zone 66 that extends beyond the location zone 56. Indicia means such as a measurement scale 68, preferably graduated in centimeters, is provided alongside the slot 54 at the location zones 56, 58, 60, 62 and 64.

The sensor locating member 14 also includes a flange portion 70 adjacent the clearance zone 66. An angle indicia 72 is provided on the flange portion 70 and a pivot opening 74 is spaced from the angle indicia 72.

When the pivot pieces 16a and 16b (FIG. 5) are passed through the pivot openings 54 and 74 to pivotally join the locating members 12 and 14, the angle indicia 72 shows through the scale opening 48.

Figure 3:
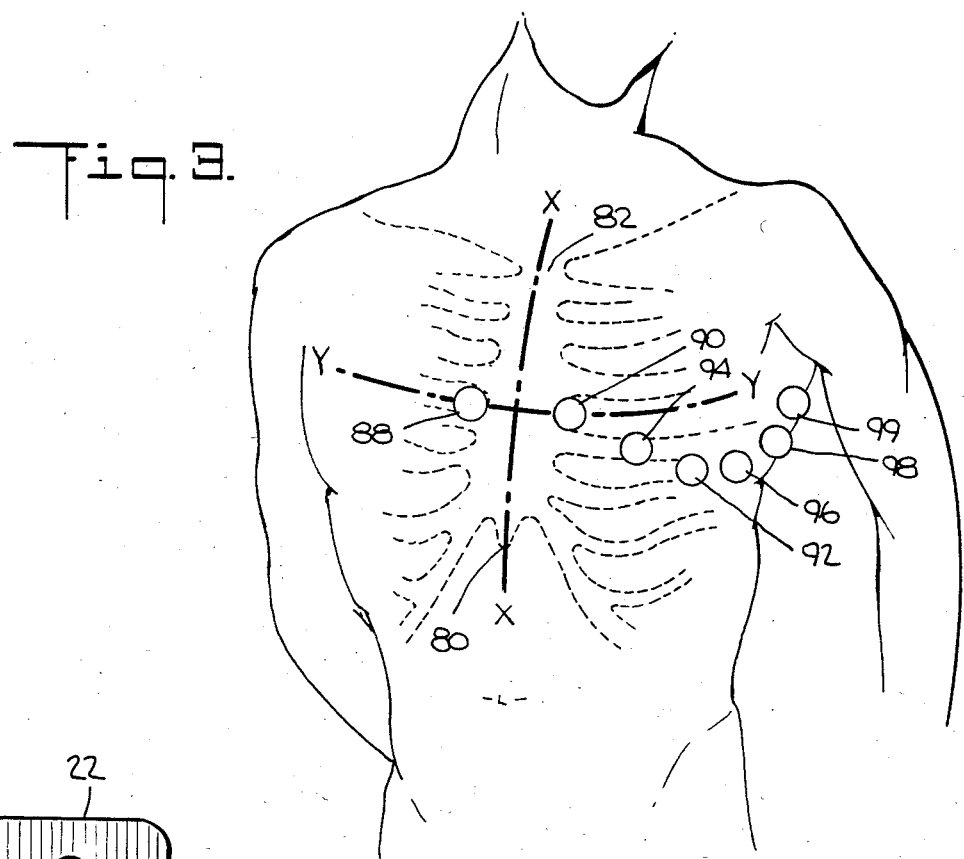
FIG. 3 is a schematic fragmentary view of the anatomical landmarks used to locate the electrocardiograph sensor positioning device.

In using the electrocardiograph sensor positioning device 10, the sensor locating member 12 is positioned according to some well known anatomical landmarks. For example, the sternal angle or sternum notch, schematically indicated at reference number 80 of FIG. 3, determines the point at which the sternum notch register 44 of the sensor locating member 12 is positioned. The clavicular notch, schematically indicated at the reference number 82 of FIG. 3 is aligned with the narrow slot 20 of the sensor locating member 12. It will be noted from FIG. 3 that a reference axis X—X can be shown to extend through the sternum notch 80 and the clavicular notch 82 to define a midclavicular line.

Once the locating member 12 has been positioned as described, the measurement scale 24 will indicate the location of the clavicular notch 82 for the particular patient being examined. A mark indicated by the arrow 84 in FIG. 4 can be made directly on the locating member 12 and thereby indicate a first identifiable characteristic of the patient being examined. The locating member 12 can be taped or otherwise secured to the patient's chest, as by tape strips 86 shown in FIG. 4.

The locating member 14 is pivoted with respect to the locating member 12 to a position wherein the location zones 58, 60 and 62 align with the fifth intercostal space to the left of the midclavicular line X—X. The sensor locating member 14 is also secured to the patient, using adhesive strips such as 86.

The angle at which the locating member 14 is pivoted with respect to the locating member 12 is read from the angle indicia scale 72 which shows through the scale opening 48 at the indicia line 50. This reading can be written directly on the flange 46, and represents a second identifiable characteristic of the patient being examined.

When the locating members 12 and 14 have been positioned on a patient, the zones 34 and 38 of the locating member 12 surround a desired zone on the patient wherein the electrocardiograph sensors will be positioned. The desired zones on the human body can be characterized as the V1 and V2 sectors as indicated on the locating member 12 (FIG. 2) alongside the zones 34 and 38.

In addition the locating member 14 when positioned on a patient locates desired sensor positioning zones on the patient's anatomy within the zones 56, 58, 60, 62 and 64. The sensor positioning zones on the human anatomy corresponding to the zones 56, 58, 60, 62 and 64 are characterized as the V3 sector, the V4 sector, the V5 sector, the V6 sector and the V7 sector, respectively as indicated on the locating member 14 (FIG. 2).

Referring to FIGS. 2, 3 and 4, the V1 sector at zone 34 locates an electrocardiograph sensor schematically shown as 88 in FIG. 3 at the right border of the sternum in the fourth intercostal space. The V2 sector locates an electrocardiograph sensor 90 at the left border of the sternum in the fourth intercostal space. The V4 sector at zone 58 locates an electrocardiograph sensor 92 at the left midclavicular line in the fifth intercostal space.

The V3 sector at zone 56 will locate an electrocardiograph sensor 94 at the left parasternal line approximately midway between the electrocardiograph sensors 90 and 92.

The V5 sector at zone 60 locates an electrocardiograph sensor 96 at the anterior axillary line at the fifth intercostal space, and the V6 sector at zone 62 will locate an electrocardiograph sensor 98 at the midaxillary line, also at the fifth intercostal space. The V7 sector at zone 64 will locate an electrocardiograph sensor 99 at the outer axillary line in the fifth intercostal space.

Once each of the electrocardiograph sensors 88-99 haVe been positioned, their locations can be marked directly on the locating members 12 and 14 by making an appropriate indication on the measurement scales 40, 42 and 68.

Under this arrangement, when an electrocardiogram examination is completed the device 10 can be given to the patient and the data that has been marked on said device can be recorded in the patient's medical records. Upon subsequent examination of the patient, the data provided by the device 10 will assure a substantially exact repeat of the location of the electrocardiograph sensors as they were positioned in the previous examination. Thus a more meaningful comparison of data obtained in a series of electrocardiograph examinations can be accomplished.

The location of the electrocardiograph sensors 88 and 90 as shown in FIG. 3, defines another reference axis Y—Y. It has been found for human anatomies which range from 24 inches in height to 84 inches in height, and from 12 inches in width through 30 inches in width, and from 6 inches in depth through 20 inches in depth, that there are approximately 7,741,440 possible sensor locations when the height, width and depth dimensions are varied by one-eighth inch increments. If the sensor locations at the V1 and V2 sectors are considered to be constant, there are still more than 387,000 possible sensor locations for the previously described size range of human anatomy.

Accordingly, in developing the device 10, individualized locating members (not shown) were prepared for a varying size range of human anatomies. The shape and size of the zones 34 and 38 of the locating member 12 represent a consensus of the various possible sensor locations for the range of body shapes previously described.

The size and shape of the locating member 14 and the pivotal capability of the locating member 14 with respect to the locating member 12 represent a similar consensus of the desired locations of electrocardiograph sensors for the range of body size previously discussed.

For example, separate templates were prepared for different body sizes. The templates were then placed on top of each other to determine the range of curvature and direction that would encompass the various limits in body size, namely the limits from the smallest body stature to the largest body stature; the smallest body width to the largest body width, and the smallest body depth to the largest body depth. Based on this collective examination of the individual templates it was found that by pivoting the locating member 14 at a predetermined pivot point as disclosed, the resulting range of movement of the locating member 14 would encompass all possible electrocardiograph sensor positions for the particular body sizes described at the V3 sector, the V4 sector, the V5 sector, the V6 sector and the V7 sector.

The electrocardiograph sensor positioning device is thus a device which is adaptable to a wide range of body sizes regardless of sex.

Although the dimensions of the electrocardiograph sensor positioning device can vary, to exemplify the magnitudes being dealt with it has been found that a feasible overall height for the locating member 12 is 27 centimeters and a feasible overall width from the zone section 28 to the zone section 30 is approximately 17.8 centimeters. The slot 20 can be approximately 10 centimeters long and spaced 11 centimeters from the sternum notch register 44. The width of the zones should be sufficient to accommodate the particular size electrocardiograph sensor being used.

A feasible overall length of the locating member 14 from terminal point to terminal point is approximately 30.5 centimeters and the overall height is approximately 11 centimeters. It has been found that a centimeter scale alongside the zones 56, 58, 60, 62 and 64 can extend from 1 to 24 centimeters.

If desired, an adjustable electrocardiograph sensor positioning device can be built according to the principles shown in FIG. 6. Accordingly, a further embodiment of the electrocardiograph sensor positioning device is generally indicated by the reference number 100 in FIG. 6. The device 100 includes a sensor locating member 102 pivotally secured to a sensor locating member 104. The sensor locating member 102 includes a main section 18 and a slidable section 106 slidably secured to the main section 18 in any suitable known fashion. The slidable section 106 includes a slot 108 continuous with the slot 20 of the main section 18. The slot 108 also includes a measurement scale 110, the readings of which can be added to the exposed portion of the measurement scale 24 of the main section 18.

The sensor locating member 104 includes a slidable section 110 slidably secured in any suitable known fashion to a pivotal section 112 that is similar in most respects to the sensor locating member 14 except for the fact that the V7 sector on the pivotal section 112 is open ended.

Once the locating member 104 is taped to the patient, a mark can be made directly thereon indicating the point at which the slidable section 110 has been extended. The graduated readings on the slidable section 110 can then be added to the graduated readings on the pivotal section 112 to ascertain the exact locations of the electrocardiograph sensors.

The V3, V4, V5, V6, V7 sectors can be indicated by appropriate abbreviations on the sensor locating member 104 and any selected mark that indicates the particular location of a sensor can be made as previously described.

It should be noted that either embodiment of the electrocardiograph sensor positioning device can be made as a disposable article intended for one time use on a single individual.

In view of the above, it will be seen that the several objects of the invention are achieved and other advantageous results attained. As various changes can be made in the above constructions and methods without departing from the scope of the invention, it is intended that all matter contained in the above description or shown in the accompanying drawings shall be interpreted as illustrative and not in a limiting sense.

What is claimed is:

1. An electrocardiograph sensor positioning device comprising, first and second sensor locating members angularly adjustable with respect to each other to a determinable angular position, cooperative indicia means on said first and second sensor locating members for providing an indication of said angular position, zone locating means on said first and second sensor locating members for defining location zones for a plurality of electrocardiograph sensors, and zone indicia means at said zone locating means for providing an indication of the respective locations of said electrocardiograph sensors when said electrocardiograph sensors are positioned in respective said location zones.

2. The device as claimed in claim 1, wherein said first and second sensor locating members are pivotable with respect to each other.

3. The device as claimed in claim 1, for use on the human anatomy having a sternal notch and a clavicular notch, wherein one of said sensor locating members includes registering means for aligning said one of said sensor locating members in a predetermined position along an imaginary line joining the sternal notch and the clavicular notch.

4. The device as claimed in claim 3, wherein said registering means includes clavicle indicia means for providing a readout of the location of said clavicular notch with respect to said sternal notch.

5. The device as claimed in claim 3, wherein said registering means includes a slot for alignment with the clavicular notch.

6. The device as claimed in claim 3, wherein said one of said sensor locating members includes an extendable section.

7. The device as claimed in claim 6, wherein said registering means includes clavicle indicia means for providing a readout of the location of said clavicle with respect to said sternal notch, the extendable section of said one of said locating members providing extension of said clavicle indicia means.

8. The device as claimed in claim 3, wherein said one sensor locating member has two of said zone locating means.

9. The device as claimed in claim 8, wherein said two zone locating means comprise curved slots having corresponding adjacent ends and respective opposite ends that diverge away from each other.

10. The device as claimed in claim 3, wherein the other of said sensor locating members includes at least one elongated slot, the confines of said slot defining the location zones for said electrocardiograph sensors.

11. The device as claimed in claim 1, wherein said first and second sensor locating members are formed of a non-conductive material.

12. An electrocardiograph sensor positioning device comprising a first locating member defining a first location path for at least one electrocardiograph sensor and a second sensor locating member moveable with respect to said first sensor locating member and defining second location path for a plurality of said electrocardiograph sensors, indicia means on said first and second sensor locating members at said first and second locating paths for providing an indication of the respective locations of said electrocardiograph sensors that are positioned along said first and second locating paths.

13. The device as claimed in claim 12, for use on the human anatomy wherein said first locating path is formed to have a first alignment with the fourth intercostal space at the right border of the sternum.

14. The device as claimed in claim 13, wherein said second locating path is formed to have a second alignment with the fifth intercostal space at the left midclavicular line and to extend along said fifth intercostal space to the outer axillary line.

15. The device as claimed in claim 14, wherein said first and second sensor locating members are pivotally joined together and said second locating path is formed to align with the left parasternal line at the fourth intercostal space when said first locating path is at the first alignment and the second locating path is at the second alignment.

16. The device as claimed in claim 14, wherein said first and second sensor locating members are formed of a flexible bendable material to conform to the human anatomy.

17. The device as claimed in claim 12, wherein said first sensor locating member includes alignment means for aligning said first sensor locating member along a reference line extending between the sternal notch and the clavicular notch.

18. A method of locating electrocardiograph sensors on the human anatomy comprising
 (a) establishing a longitudinal reference between the clavicular notch and the sternal notch,
 (b) fixing the origin of the longitudinal reference at the sternal notch,
 (c) establishing a first plurality of location zones for the sensors as a result of the establishing of the longitudinal reference and the fixing of the origin of the longitudinal reference,
 (d) establishing a second reference path that extends from one of the first plurality of locating zones along one of the intercostal spaces, and
 (e) defining a second plurality of locating zones for the electrocardiograph sensors along the second reference path.

19. The method of claim 18, including the use of a pair of templates to establish the location of the first and second reference paths.

20. The method of claim 19, including marking the positions of the electrocardiograph sensors directly on the templates.

* * * * *